(12) United States Patent
Sackler et al.

(10) Patent No.: US 7,790,215 B2
(45) Date of Patent: Sep. 7, 2010

(54) SUSTAINED-RELEASE GEL COATED COMPOSITIONS

(75) Inventors: Richard S. Sackler, Greenwich, CT (US); Benjamin Oshlack, New York, NY (US); Curtis Wright, Norwalk, CT (US)

(73) Assignee: Purdue Pharma LP, Stamford, CT (US)

( * ) Notice: Subject to any disclaimer, the term of this patent is extended or adjusted under 35 U.S.C. 154(b) by 1541 days.

(21) Appl. No.: 10/401,111

(22) Filed: Mar. 26, 2003

(65) Prior Publication Data

US 2003/0190362 A1   Oct. 9, 2003

Related U.S. Application Data

(60) Provisional application No. 60/367,832, filed on Mar. 26, 2002.

(51) Int. Cl.
*A61J 3/00*   (2006.01)
(52) U.S. Cl. ..................................... 427/2.21
(58) Field of Classification Search ................. 424/464; 427/2.21, 221
See application file for complete search history.

(56) References Cited

U.S. PATENT DOCUMENTS

| | | | | |
|---|---|---|---|---|
| 3,959,540 A | 5/1976 | Leiberich et al. | ............... | 428/35 |
| 4,350,679 A | 9/1982 | Mizuno et al. | ................. | 424/38 |
| 4,432,768 A | 2/1984 | Brown et al. | ................. | 604/200 |
| 4,820,524 A | 4/1989 | Berta | ......................... | 424/474 |
| 5,114,720 A * | 5/1992 | Becker | ....................... | 424/478 |
| 5,146,730 A | 9/1992 | Sadek et al. | ................... | 53/454 |
| 5,200,191 A | 4/1993 | Steele et al. | ................. | 424/453 |
| 5,459,983 A | 10/1995 | Sadek et al. | ................... | 53/560 |
| 5,653,993 A | 8/1997 | Ghanta et al. | | |
| 5,695,784 A * | 12/1997 | Pollinger et al. | ............. | 424/495 |
| 5,827,535 A | 10/1998 | Stone | .......................... | 424/451 |
| 6,143,353 A * | 11/2000 | Oshlack et al. | ............. | 427/2.21 |
| 6,183,845 B1 | 2/2001 | Ikemoto | ...................... | 428/213 |
| 6,193,999 B1 | 2/2001 | Gennadios | ................... | 424/456 |
| 6,277,384 B1 | 8/2001 | Kaiko et al. | | |
| 6,475,494 B2 * | 11/2002 | Kaiko et al. | .................. | 424/400 |
| 2003/0017222 A1 | 1/2003 | Yanagisawa et al. | | |
| 2008/0063779 A1 | 3/2008 | Macquarrie | | |

FOREIGN PATENT DOCUMENTS

| | | |
|---|---|---|
| EP | 0076515 A1 | 10/1982 |
| EP | 0419121 B | 3/1991 |
| JP | S50-142476 | 11/1975 |
| JP | S55-136061 | 10/1980 |
| JP | S58-58145 | 4/1983 |
| JP | S58-138458 | 8/1983 |
| JP | 2002-338501 | 11/2002 |
| WO | WO 00/48574 A1 | 8/2000 |
| WO | WO01/058447 | 8/2001 |

OTHER PUBLICATIONS

Rowe et al., Hanbook of Pharmaceutical Excipients, pp. 297-300, (2003).

* cited by examiner

*Primary Examiner*—Johann R Richter
*Assistant Examiner*—Ali Soroush
(74) *Attorney, Agent, or Firm*—Davidson, Davidson & Kappel, LLC

(57) ABSTRACT

Disclosed in certain embodiments is a coating comprising a pharmaceutically acceptable mixture of gelatin and hydrophobic polymer.

77 Claims, No Drawings

SUSTAINED-RELEASE GEL COATED COMPOSITIONS

This application claims the benefit of U.S. Provisional Application Ser. No. 60/367,832 filed Mar. 26, 2002, hereby incorporated by reference.

BACKGROUND OF THE INVENTION

The present invention relates to sustained-release gel coatings and to sustained release pharmaceutical compositions containing gel coatings.

Sustained-release preparations provide a longer duration of pharmacological response after administration than is ordinarily experienced after the administration of an immediate release dosage form. Such longer periods of response provide for therapeutic benefits that are not achieved with shorter acting, immediate release products.

Gelatin and gel coatings have been utilized in the filed of pharmaceutical dosage forms. For example, empty gelatin capsules are used for encapsulating active medicaments to create unit dosages and to facilitate swallowing of the dosage form. Gelatin capsules may be produced from gelatin-glycerin, pure gelatin, sugar gelatin, or other soluble gelatin combinations. Certain gel coatings (e.g., soft gel capsules) can be prepared by adding glycerin or sorbitol to a gelatin shell to render the gelatin elastic or plastic-like (Ansel, Howard C., *Introduction to Pharmaceutical Dosage Forms*, $4^{th}$ edit., p. 136, 1985. Other gel coatings (e.g., hard gelatin capsules) are utilized to provide for a more esthetic easier to swallow dosage form. U.S. Pat. Nos. 3,959,540; 4,350,679; 4,820,524; 5,459,983; 6,183,845 and 6,193,999 relate to pharmaceutical dosage forms with gel coatings.

There exists a need in the art for sustained-release gel coatings and for sustained release compositions containing gel coatings All documents cited herein, including the foregoing, are incorporated by reference in their entireties for all purposes.

SUMMARY OF THE INVENTION

It is an object of the invention to provide sustained-release gel coated compositions.

It is an object of certain embodiments of the invention to provide an oral sustained-release dosage form comprising an active agent coated with a sustained-release gel coating, wherein the gel coating provides for the sustained-release of the active agent from the dosage form.

It is an object of certain embodiments of the present invention to provide an oral sustained-release dosage form, wherein a sustained-release matrix or sustained-release core containing an active agent is overcoated with a sustained-release gel coating to provide additional sustained-release properties to the dosage form.

It is an object of certain embodiments of the present invention to provide an oral dosage form comprising: (i) an opioid agonist; and (ii) an opioid antagonist in the form of multiparticulates individually coated with a coating comprising gelatin optionally mixed with a hydrophobic polymer.

It is an object of certain embodiments of the present invention to provide a method of decreasing the abuse potential of an opioid agonist in a sustained release composition comprising preparing an oral sustained-release composition with a gel coating, wherein the gel coating is capable of inhibiting attempts to tamper with the dosage form.

These objects and others are accomplished by the present invention, which relates in part to a coating comprising a pharmaceutically acceptable mixture of gelatin and hydrophobic polymer, wherein the hydrophobic polymer is present in an amount of at least 20% based on the total weight of the coating.

In other embodiments, the present invention is directed to a coating comprising a pharmaceutically acceptable mixture of gelatin and acrylic polymer.

In other embodiments, the present invention is directed to an oral pharmaceutical dosage form comprising active agent and a coating disposed about the active agent, wherein the coating comprises a pharmaceutically acceptable mixture of gelatin and hydrophobic polymer, and the hydrophobic polymer is present in an amount of at least 20% based on the total weight of the coating.

In other embodiments, the present invention is directed to an oral pharmaceutical dosage form comprising active agent and a coating disposed about the active agent, wherein the coating comprises a pharmaceutically acceptable mixture of gelatin and acrylic polymer.

In other embodiments, the present invention is directed to an oral pharmaceutical dosage form comprising a plurality of inert beads, a first layer comprising active agent disposed about the inert beads, and a second layer comprising a pharmaceutically acceptable mixture of gelatin and hydrophobic polymer disposed about the first layer.

In other embodiments, the present invention is directed to a pharmaceutical composition comprising an inert core, a first layer and a second layer, the first layer being between the core and the second layer, the first layer comprising an opioid antagonist and the second layer comprising a mixture of gelatin and hydrophobic polymer.

In other embodiments, the present invention is directed to a pharmaceutical composition comprising an inert core, a first layer, a second layer and a third layer, the first layer being between the core and the second layer, the second layer being between the first layer and the third layer, the first layer comprising an opioid antagonist, the second layer comprising a hydrophobic polymer and the third layer comprising a mixture of gelatin and hydrophobic polymer.

In other embodiments, the present invention is directed to a pharmaceutical dosage form comprising a sustained release substrate comprising a matrix comprising an opioid agonist; and a coating comprising gelatin disposed about the substrate.

In other embodiments, the present invention is directed to an oral pharmaceutical dosage form comprising a plurality of inert beads, a first layer comprising an active agent selected from the group consisting of an opioid agonist, an opioid antagonist and a mixture thereof, the active agent disposed about the inert beads, a second layer comprising a hydrophobic material disposed about the first layer, and a third layer comprising gelatin disposed about the second layer.

In other embodiments, the present invention is directed to an oral pharmaceutical dosage form comprising a plurality of matrices comprising an active agent selected from the group consisting of an opioid agonist, an opioid antagonist and a mixture thereof, the active agent at least partially interdispersed in a hydrophobic polymer; and a layer comprising gelatin disposed about the matrices.

In other embodiments, the present invention is directed to a pharmaceutical composition comprising about 10 mg oxycodone hydrochloride, less than about 5.0 mg naltrexone hydrochloride, gelatin and a hydrophobic polymer, wherein the gelatin and the hydrophobic polymer are optionally at least partially interdispersed.

In other embodiments, the present invention is directed to a pharmaceutical composition comprising a first component comprising about 10 mg oxycodone hydrochloride; and a second component comprising less than about 5.0 mg naltrexone hydrochloride, gelatin and a hydrophobic polymer, wherein the gelatin and the hydrophobic polymer are optionally at least partially interdispersed.

In other embodiments, the present invention is directed to a pharmaceutical composition comprising about 20 mg oxycodone hydrochloride, less than about 5.0 mg naltrexone hydrochloride, gelatin and a hydrophobic polymer, wherein the gelatin and the hydrophobic polymer are optionally at least partially interdispersed.

In other embodiments, the present invention is directed to a pharmaceutical composition comprising a first component comprising about 20 mg oxycodone hydrochloride; and a second component comprising less than about 5.0 mg naltrexone hydrochloride, gelatin and a hydrophobic polymer, wherein the gelatin and the hydrophobic polymer are optionally at least partially interdispersed.

In other embodiments, the present invention is directed to a pharmaceutical composition comprising about 40 mg oxycodone hydrochloride, less than about 5.0 mg naltrexone hydrochloride, gelatin and a hydrophobic polymer, wherein the gelatin and the hydrophobic polymer are optionally at least partially interdispersed.

In other embodiments, the present invention is directed to a pharmaceutical composition comprising a first component comprising about 40 mg oxycodone hydrochloride; and a second component comprising less than about 5.0 mg naltrexone hydrochloride, gelatin and a hydrophobic polymer, wherein the gelatin and the hydrophobic polymer are optionally at least partially interdispersed.

In other embodiments, the present invention is directed to a pharmaceutical composition comprising about 5-20 mg hydrocodone bitartrate, less than about 5.0 mg naltrexone hydrochloride, gelatin and a hydrophobic polymer, wherein the gelatin and the hydrophobic polymer are optionally at least partially interdispersed.

In other embodiments, the present invention is directed to a pharmaceutical composition comprising a first component comprising about 5-20 mg hydrocodone bitartrate, and a second component comprising less than about 5.0 mg naltrexone hydrochloride, gelatin and a hydrophobic polymer, wherein the gelatin and the hydrophobic polymer are optionally at least partially interdispersed.

In other embodiments, the invention is directed to a method of preparing the dosage forms as disclosed herein.

In other embodiments, the invention is directed to a method of treating a patient comprising administering to the patient a dosage form as disclosed herein comprising a drug indicated for the treatment (e.g., an opioid analgesic for a patient in pain).

In other embodiments, the invention is directed to a kit comprising a dosage form as disclosed herein comprising a drug and instructions (e.g., printed instructions) for using the dosage form.

Although the present invention has been disclosed with respect to oral dosage forms, in certain embodiments, the invention is directed to any dosage forms which can be administered with a gel coating (e.g., rectal and intravaginal dosage forms).

The term "coating" includes a layer disposed about a substrate, e.g., an inert bead or a previously coated bead. Coating of substrates can be performed by procedures known in the art, e.g., spray coating, dipping or enrobing with a gelatin coat as described in U.S. Pat. Nos. 3,959,540; 4,350,679; 4,432,768; 4,820,524; 5,146,730; 5,200,191; 5,459,983; 5,827,535; 6,183845; and 6,193,999.

The term "disposed about" means that the substance disposed about the substrate covers at least a portion of the substrate, with or without an intermediate layer or layers between the substance and the substrate.

DESCRIPTION OF THE INVENTION

The materials used to provide for the sustained-release gel coatings of the present invention include gelatins, hydrophobic polymers, and optional pharmaceutically acceptable ingredients such as plasticizers, colorants, preservatives and opacifying agents. The gelatin is preferably derived from a partial hydrolysis of collagen, which is obtained from skin, connective tissue and bones of animals (Ansel, Howard C., Introduction to Pharmaceutical Dosage Forms, $4^{th}$ edit., p. 126, 1985). The gelatin of the present invention may be prepared, e.g., from a mixture containing about 40% by weight bone (150 bloom), about 20% by weight hyde (245 bloom), and about 40% pork skin (270 bloom). This mixture has a viscosity of 500 cp as measured by a Brookfield Chromatograph, at an operating temperature of 130° F. The viscosity of the gelatin affects the thickness of the gel coating.

Preferably the coating thickness ranges from about 5 to 50 mils (thousandths of an inch), more preferably about 10 to 30 mils and most preferably about 15 to 25 mils. The coating thickness is can be modified to provide various changes in the property of the sustained-release gel coated dosage form, e.g., duration of sustained-release or smoother, easier to swallow dosage forms. Generally, an increase in hydrophobic material will increase sustained-release and an increase in gelatin will increase smoothness.

Gelatin source materials affect the elasticity of the films, and the ability of the films to adhere to the tablet, capsule or core substance containing the active agent. Preferably the sustained-release gelatin coatings of the present invention can either: (i) directly adhere to the core substance, thereby becoming an integral part of the dosage formulation, or (ii) the sustained-release gel coating can enrobe the core substance to provide an adhering effect, whereby only certain portions of the outer surface of the active agent are in contact with the sustained-release gel coating. The former effect is preferred because a sustained-release gel coating that directly adheres to the core substance provides for a more tamper-resistant dosage form, e.g., in sustained-release opioid formulations, the coating will be more difficult to "scratch off" in an attempt or a perceived attempt to remove the sustained-release coating in order to provide an immediate release of the active agent therein.

In certain embodiments the active agent is an opioid agonist and is included in a sustained-release substrate comprising a sustained release matrix, an immediate release matrix with a sustained release coating, or a sustained release matrix with a sustained release coating. In such embodiments, the gelatin coating which is difficult to "scratch off" in an attempt to liberate and provide an immediate release of the opioid contained therein, may be an immediate release gelatin coating which does not provide any significant sustained-release properties to the opioid contained in the substrate. Thus, when the active agent is an opioid agonist in sustained release form, the gel coating of the present invention can be an immediate release gelatin coating or a sustained-release gelatin coating comprising gelatin and a hydrophobic polymer as disclosed herein. The sustained release opioid substrate is preferably in the form of at tablet and the gelatin coating can have a thickness from about 5 to 100 mils, from about 60 to 100 mils or from about 15 to 40 mils. Optionally, a film coating, e.g., hydroxypropylmethylcellulose, can be applied between the matrix and the gel coating, the matrix and the sustained release coating, or the sustained release coating and gel coating.

In certain embodiments, the hydrophobic polymer is a cellulosic polymer, including but not limited to cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate, cellulose acetate butyrate and mixtures thereof. Preferably, the cellulosic polymer is an alkyl cellulosic polymer such as ethylcellulose.

In other embodiments of the present invention, the hydrophobic polymer is a pharmaceutically acceptable acrylic polymer, including but not limited to acrylic acid and methacrylic acid copolymers, methacrylic acid copolymers, methyl methacrylate copolymers, ethoxyethyl methacrylates, cyanoethyl methacrylate, methyl methacrylate, copolymers, methacrylic acid copolymers, methyl methacrylate copolymers, methyl methacrylate copolymers, methyl methacrylate copolymers, methacrylic acid copolymer, aminoalkyl methacrylate copolymer, methacrylic acid copolymers, methyl methacrylate copolymers, poly(acrylic acid), poly(methacrylic acid, methacrylic acid alkylamide copolymer, poly (methyl methacrylate), poly(methacrylic acid) (anhydride), methyl methacrylate, polymethacrylate, methyl methacrylate copolymer, poly(methyl methacrylate), poly(methyl methacrylate) copolymer, polyacrylamide, aminoalkyl methacrylate copolymer, poly(methacrylic acid anhydride), glycidyl methacrylate copolymers and mixtures of any of the foregoing.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

The hydrophobic polymer can be one or more cellulosic polymer and one or more acrylic polymer. The hydrophobic polymer of the present invention is preferably in an amount from about 20% to about 99%, preferably from about 20% to about 80%, and most preferably from about 40% to about 60% by weight, based on the dry weight of the sustained-release gel coating.

In certain embodiments of the present invention the sustained-release gel coating may comprise a hydrophobic component derived from an aqueous dispersion of a hydrophobic polymer. The inclusion of an effective amount of a plasticizer in the aqueous dispersion of hydrophobic polymer will further improve the physical properties of the gel coating. For example, because ethylcellulose has a relatively high glass transition temperature (Tg) and does not form flexible films under normal coating conditions, it is necessary to plasticize the ethylcellulose before using the same in a gel coating. The glass transition temperature is related to the temperature or temperature range where there is a fundamental change in the physical properties of the polymer. This change does not reflect a change in state, but rather a change in the macromolecular mobility of the polymer. Below the Tg, the polymer chain mobility is severely restricted. Thus, for a given polymer, if its Tg is above room temperature, the polymer will behave as a glass, being hard, non-pliable and rather brittle, properties which could be somewhat restrictive in gel coating since the coated dosage form may be subjected to a certain amount of external stress.

Incorporation of suitable plasticizers into the gel coating effectively reduces the Tg, so that under ambient conditions the gel coatings are softer, more pliable and often stronger, and thus better able to resist mechanical stress.

The suitability of a plasticizer depends on its affinity or solvating power for the hydrophobic polymer and its effectiveness at interfering with polymer-polymer attachments. Such activity imparts the desired flexibility by relieving molecular rigidity. Generally, the amount of plasticizer included in a coating solution is based on the concentration of the gelatin, e.g., in an amount from about 1 to about 50 percent by weight of the gelatin. Concentration of the plasticizer, however, can only be properly determined after careful experimentation with the particular coating solution and method of application. The use of a plasticizer may improve the gel coating elasticity and lower the film-forming temperature of the gel coating. The plasticization of the gel coating may be accomplished either by so-called "internal plasticization" and "external plasticization." Most preferably, about 5-12% plasticizer is included in the sustained-release gel coating, based on the dry weight of the gel coating.

Internal plasticization usually pertains directly to molecular modifications of the hydrophobic polymer during its manufacture, e.g., by copolymerization, such as altering and/or substituting functional groups, controlling the number of side chains, or controlling the length of the hydrophobic polymer. Such techniques are usually not performed by the formulator of the coating solution.

External plasticization involves the addition of a material to a gel coating solution so that the requisite changes in gel coating properties of the dry gel coat can be achieved.

Plasticizer materials used in the sustained-release gel coating of the present invention include hygroscopic plasticizers such as glycerin, sorbitol, and alkylene glycols (e.g., propylene glycol and low molecular weight polyethylene glycols); non-hygroscopic plasticizers (e.g., maltitol, lactitol, xylitol, hydrogentated starch hydrolysate and partially dehydrated hydrogenated glucose syrups); diethyl phthalate, citric acid, mineral oil and lanolin alcohols, and petrolatum and lanolin alcohols. The ratio of plasticizer to gelatin in the sustained-release gel coating is preferably from about 1:3 to 1:15, preferably about 1:5. When the ratio of plasticizer to gelatin in the dosage form is low, the sustained-release gel coating enrobing the core substance can be brittle, whereas a higher ratio of plasticizer to gelatin results in a more elastic and flexible coating around the core substance.

In certain embodiments, the sustained-release gel coating of the present invention may contain from about 30 to 60% gelatin, from about 20 to 80% hydrophobic polymer, from about 5 to 35% plasticizer, an amount of water and from about 0.1 to 3% of a pharmaceutically acceptable ingredient selected from the group consisting of a colorant, a preservative, an opacifying agent and mixtures of any of the foregoing, based on the dry weight of the gel coating. Once prepared, the subsequent sustained-release gel coated dosage forms are dried to an approximate moisture content e.g., from about 5-10%, by weight or less than 5%.

The sustained-release gel coatings of the present invention can be applied to the active agent, for example, by the die method. One particular use of the die process and apparatus are described in U.S. Pat. No. 5,146,730. The manufacturing process and equipment create and use a first and second film of soft elastic gelatin of selected thickness and composition, and a pair of matching dies (which preferably are rotary dies)

and between which films pass adjacent the location where a core feed device cooperates with at least one and preferably both of the films and dies. The sustained-release gel coated dosage forms of the present invention are preferably made by use of an appropriately arranged apparatus pursuant to processes in which the cores of the dosage form are initially engaged with only one of the two films before the films come together between matching dies. However, the core feeding mechanism may be arranged to introduce the cores to the films in the working area between the dies so that each core contacts both films essentially simultaneously.

The gelatin films, including a hydrophobic material, are individually cast on separate rotating casting drums in a continuous manner by introduction of a liquid including gelatin and a hydrophobic polymer, to the outer casting surface of each drum from a liquid dispensing device and to which the suitably prepared liquid of appropriate formulation is supplied. The liquid may preferably be supplied to each dispensing device from a respective container in which the gelatin/hydrophobic polymer liquid is kept liquid at an elevated temperature by a heater, such as an electrical heater. Each container is airtight so that liquid can be moved from the interior of the container to the adjacent dispensing device through a transfer tube under the effect of compressed air introduced to the container through an inlet tube. Gravity feed of the liquid to the dispensing devices can be used, if desired.

Each casting drum may preferably be cooled by circulation of an appropriate coolant as a result of which the casting surface of the drum may preferably be substantially colder than the liquid gelatin/hydrophobic polymer as introduced to the surface of the rotating casting drum by the dispensing device.

Hence, the liquid gelatin/hydrophobic polymer introduced to the moving casting surface as a layer of sustained-release film of predetermined thickness solidifies on the drum casting surface sufficiently to form the films adequately so that the films can be led continuously from the respective casting drum to dies along a desired path. The path of movement of the cast gelatin/hydrophobic polymer film is through a lubricant bath via a roller and thence to a driven tractor roll. The lubricant in the bath is preferably applied in the bath principally to the reverse surface of the film, i.e., the surface of the gelatin/hydrophobic polymer film which will not be contacted with the other film when the two films come in contact with each other between the die rolls. The outer surface of a tractor roll may preferably be enwrapped by a traction layer in the form of a sleeve of elastomeric mesh which enables the traction layer to co-act without slippage with the reverse surface of the film passing over the traction roll despite the presence on that film surface of a thin layer of lubricant. Thus, as the film passes from each tractor roll to the adjacent die, a thin layer of lubricant remains on the reverse surface of the gelatin/hydrophobic polymer film to function between the film and the cooperating die to prevent the die and the film from sticking to each other as the die operates upon the film engaged with it in the manner described more fully below.

In a preferred process the dies, together with the cooperating portion of the core feed mechanism, are symmetrically disposed relative to each other about a functional center plane of the apparatus. The portion of the core feed mechanism immediately adjacent to the cooperating dies is a core feed horn disposed upon a functional center plane in association with and between a pair of shaped metal heater blocks which extend across the width of the adjacent gelatin/hydrophobic polymer film. Each heater block preferably includes therein an electrical resistance heater element for controllably heating the heater blocks. The heater blocks are provided in close proximity to the core feed horn and to the die rolls for contacting the obverse surface of the adjacent film in that portion of the film path where the film may preferably be wrapped around the adjacent die roll. The heater blocks heat the gelatin film obverse surface to a desired temperature which is important to the topics of self-timing operation of the dies and feed mechanism and of the character of the enrobement of each product core by the films.

Accordingly, each heater block has a curved film-contacting surface configured for contact with the obverse surface of the moving gelatin film as it conforms to the outer diameter of the adjacent preferably rotary die as closely as possible to the point at which individual product cores emerge from the lower end of the wedge-shaped lower portion of core feed horn substantially at the nip of the dies. The die nip is the place where the films are brought into contact with each other by the dies, i.e., the place along the film paths where the dies contact with each other to enrobe the tablet cores (product preforms) with the films, to seal the films together around the individual cores, and to cut the enrobed cores from the film which are then mated to each other. Forms of film heating arrangements different from those described above can be used, if desired.

At the location in the apparatus where the die rolls and the core feed horn cooperate closely with each other, the product cores are individually contacted with the controllably heated obverse surfaces of the converging films. The films are stretched around the opposite sides of the cores symmetrically relative to apparatus center plane, thereby to define the applied layers of the coating of the desired product. The films are sealed to each other along a seam line of the product and the thus conjoined and adhered films are cut to allow the film enrobed products to separate from a perforated film web which emerges from between the dies. A web is formed by the adherence of the films to each other by the dies. After emerging from between the dies, the web passes between a pair of driven mangle rolls which have surface speeds slightly greater than the surface speeds of the dies so that the web is stretched between the dies and the mangle rolls. This stretching of the web as it exits from between the dies enables the film enrobed product cores to self-separate from the web and to move, with the assistance of product guides (cooperating with the web between the dies and the mangle roles), into a product receptacles where the products are collected before undergoing such further processing as may be necessary. Further processing steps may include washing of products to remove any residues of lubricant applied to the films in the baths or final drying.

Another process that can be used to apply the sustained-release gel coatings of the present invention to the active agent is described in U.S. Pat. No. 4,820,524. This process is accomplished by providing a holding means having a channel defined therein to hold the active agent, e.g., in caplet form, and inserting a first end of a caplet into the caplet channel while leaving the second end of the caplet exposed. The holding means is then manipulated relative to a bath of gelatinous coating to dip the second exposed end of each caplet into the bath. The resulting gelatinous coating on the second exposed end of the caplet is then permitted, and preferably caused, to dry to form a coated end. During the drying process the caplet may be rotated to assist in uniformly distributing gelatin during drying. Once dry, the coated (second) end of the caplet is then displaced through the caplet channel to expose its uncoated first end. A gelatinous coating is then applied to the uncoated first end of said caplet. The coating applied to the first end of the caplet is then permitted (or preferably caused) to dry, again with rotation if desired for the purpose of spreading the coating evenly. In a preferred process, the baths of gelatinous coating into which the caplet ends are dipped may be of different colors, to thereby create a simulated 2-piece capsule look to the finished caplets with seams about their transverse axes.

The apparatus of this process, includes bars having a plurality of cylindrical holding means mounted thereon. Each holding means receives, retains and facilitates the transfer of an individual caplet. The apparatus is fitted with a caplet feeder to feed caplets into each holding means. The holding means may, for example, be a cylinder which is open at both ends and which comprises a retaining means, such as "O"-rings or a spring biased retainer for the purpose of holding each caplet in position during the dipping process. The feeding means is preferably associated with an inserting means, which may be a simple channel and plunger assembly, for inserting a first end of each caplet into an appropriate holding means. The feeding means ensures that each caplet is inserted a sufficient distance to cause the second end of the caplet to appropriately protrude therefrom during the upcoming dipping process. Once each bar is loaded with caplets, it then proceeds to a dip station where the gelatinous coating is applied to the exposed ends of the caplets protruding there from, whereupon the bar is rotated through a first drying means for permitting the gelatinous coating to dry to form a coated second end. In a preferred embodiment apparatus, the second gripping means also comprise substantially cylindrical holders which are open at both ends, having central bores defined there through. In this embodiment, these second holders are axially aligned with the bores of the first holders, at the transfer positions, whereupon a plunger or other means is used to displace the half-coated caplets through and out of the "backs" of the firs holders and into the "backs" of the second holders, and then through the second holders until the remaining uncoated ends of the caplets are exposed for subsequent dipping. The dipping and drying processes are then repeated (preferably with a different colored gelatinous coating), whereupon a caplet ejection means pushes the caplets out of the second holders.

In another aspect of this process, the "fronts" of the second holder means are aligned with the "fronts" of the first holder means, whereupon the caplets are mechanically transferred from the first to the second holders without the need for an additional alignment device. A single holding means is used for dipping both ends of the caplet, whereby, after dipping the second end, the caplet is transferred through this single holding means to expose the uncoated first end. This holder is then shifted to the second gelatinous coating bath which preferably contains a different color gelatin for dipping the first end of the caplet. Although this process is exemplified with a caplet, it is understood that the process can be used for the active agent in other forms, e.g., a tablet.

In certain embodiments of the invention, the gelatin/hydrophobic polymer coating can be utilized in the manufacture of soft gel formulations which are prepared, e.g., according to the plate method. The plate method involves placing a warm sheet of the sustained-release gelatin coat on the bottom plate of a mold. A liquid substance comprising the active agent is evenly poured on top of the sheet of gelatin. A second sheet of the sustained-release gelatin coat is carefully placed on top of the active agent, and the top plate of the mold is put into place. The mold is subjected to pressure, whereby the sustained-release gel coated formulation is formed, filled and sealed simultaneously.

When the sustained-release gel coatings of the present invention provide for a hard gelatin capsule, several filling techniques may be utilized. For example, in the pharmacy practice setting, a pharmacist will usually use a "punch method" for filling the sustained-release gelatin capsules. This method is beneficial when the active medicament is in powder form. The powder is evenly distributed and packed down onto a sterile surface, e.g., counter top or glass/porcelain plate. The body portion of the empty sustained-release gelatin capsule is held in hand and "punched" down into the powder repeatedly until the body of the capsule is filled. Once the body of the capsule is filled, it is capped using a top portion of the sustained-release gelatin capsule. The top portion of the capsule is secured to the body portion using different techniques. In one particular example, the top portion and body portion of the sustained-release gelatin capsule are notched so that they lock together when the top portion is pushed down over the body portion of the capsule. These specific innovations in capsule design are known in the art as Snap-Fit™, Coni-Snap™, and Coni-Snap Supro™ hard gelatin capsules. Other techniques for sealing the two portions of the sustained-release gelatin capsules include applying a gelatin seal around the seam that forms between the top portion and the body portion of the capsule.

When the active medicament is in the form of a granular material, the capsules may be filled by pouring the granular material into the body portion of the sustained-release gel coated capsule prior to the top portion of the capsule being placed and sealed.

The active agent of the present invention can be in the form of, e.g., tablets, capsules, caplets, spheroids, inert beads, microspheres, seeds, pellets, ion-exchange resin beads, or other multi-particulate systems prior to being coated with the gel coating of the present invention. Granules, spheroids, or pellets, etc., can be presented in a capsule or in any other suitable dosage form. The tablets, capsules or caplets of the present invention may be any suitable shape, such as round, oval, biconcave, hemispherical, any polygonal shape such as square, rectangular, and pentagonal, and the like.

The sustained-release gel coated formulations of the present invention may be obtained by overcoating the active agent with a sufficient amount of the sustained-release gel coating to obtain a dry weight gain level from about 2 to about 25% of the total dosage form, although the gel coating may be lesser or greater depending upon, e.g., the physical properties of the active agent and the desired release rate, the inclusion of plasticizer in the gel coating and the manner of incorporation of the same. In certain embodiments of the invention, the sustained-release gel coating may be applied to the active agent up to, e.g., a 50% dry weight gain. "Dry weight" refers to the final dosage form intended for administration after drying of the coating. This definition does not exclude the possibility of residual moisture which may be retained in the coating.

The active agent may be prepared, e.g. by dissolving the therapeutically active agent in water and then spraying the solution onto a substrate, for example, nu pariel 18/20 beads, using a Wurster insert. Optionally, additional ingredients are added prior to gel coating the beads in order to assist the active agent binding to the beads, and/or to color the solution, etc. For example, a product which includes hydroxypropylmethylcellulose, with or without colorant may be added to the solution and the solution mixed (e.g., for about 1 hour) prior to application of the same onto the beads. The resultant coated active agent may then be optionally overcoated with a barrier agent to separate the therapeutically active agent from the controlled-release gel coating. An example of a suitable barrier agent is one which comprises hydroxypropylmethylcellulose. However, any film-former known in the art may be used. It is preferred that the barrier agent does not affect the dissolution rate of the final product.

The active agent, HPMC protected (optional) beads are then overcoated with a sustained-release gel coating. The gel coating preferably includes an effective amount of plasticizer, e.g. triethyl citrate. Pre-formulated aqueous dispersions of ethylcellulose, such as Aquacoat™ or Surelease™, may be used in the gel coating. If Surelease™ is used, it is not necessary to separately add a plasticizer. Alternatively, preformulated aqueous dispersions of acrylic polymers such as Eudragit™ can be used.

The gel coating solutions of the present invention preferably contain, in addition to gelatin, hydrophobic polymer, plasticizer, and water, a colorant to provide elegance and product distinction. Color may be added to the solution of the therapeutically active agent instead, or in addition to the sustained-release gel coating. For example, color may be added to Aquacoat™ via the use of alcohol or propylene glycol based color dispersions, milled aluminum lakes and opacifiers such as titanium dioxide by adding color with shear to water soluble polymer solution and then using low shear to the plasticized Aquacoat™. Alternatively, any suitable method of providing color to the formulations of the present invention may be used. Suitable ingredients for providing color to the formulation when the hydrophobic polymer is an acrylic polymer, include titanium dioxide and color pigments, such as iron oxide pigments. The incorporation of pigments, may, however, increase the retardant effect of the gel coating.

A wide variety of therapeutically active agents can be used in conjunction with the present invention. The therapeutically active agents (e.g. pharmaceutical agents) which may be used in the compositions of the present invention include both water soluble and water insoluble drugs. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), non-steroidal anti-inflammatory agents (e.g., naproxyn, diclofenac, indomethacin, ibuprofen, sulindac), anti-emetics (e.g., metoclopramide), anti-epileptics (e.g., phenytoin, meprobamate and nitrezepam), vasodilators (e.g., nifedipine, papaverine, diltiazem and nicardipine), anti-tussive agents and expectorants (e.g., codeine phosphate), anti-asthmatics (e.g. theophylline), antacids, anti-spasmodics (e.g., atropine, scopolamine), antidiabetics (e.g., insulin), diuretics (e.g., ethacrynic acid, bendrofluazide), anti-hypotensives (e.g., propranolol, clonidine), antihypertensives (e.g, clonidine, methyldopa), bronchodilators (e.g., albuterol), steroids (e.g., hydrocortisone, triamcinolone, prednisone), antibiotics (e.g., tetracycline), antihemorrhoidals, hypnotics, psycho-tropics, antidiarrheals, mucolytics, sedatives, decongestants, laxatives, vitamins, stimulants (including appetite suppressants such as phenylpropanolamine), as well as salts, hydrates, and solvates of the same. The above list is not meant to be exclusive.

In certain preferred embodiments, the therapeutically active agent comprises an opioid analgesic, e.g., hydromorphone, tramadol, oxycodone, dihydrocodeine, codeine, dihydromorphine, morphine, buprenorphine, oxymorphone, hydrocodone, salts, hydrates and solvates of any of the foregoing, mixtures of any of the foregoing, and the like.

In embodiments wherein the active agent is an opioid agonist in sustained release form with an immediate release gel coating, the herein disclosed methods of applying sustained release gel coatings may be utilized to apply immediate release gel coatings (without the inclusion of an effective amount of a hydrophobic polymer) to the sustained-release opioid substrate.

In other preferred embodiments, the agent is an opioid antagonist, e.g., naltrexone, naloxone, nalmephene, cyclazocine, levallorphan, salts, hydrates and solvates of any of the foregoing, mixtures of any of the foregoing, and the like.

In another embodiments of the present invention, the active agent is a locally active therapeutic agent and the environment of use may be, e.g., the gastrointestinal tract, or body cavities such as the oral cavity, periodontal pockets, surgical wounds, the rectum or vagina.

The locally active pharmaceutical agent(s) include antifungal agents (e.g., amphotericin B, clotrimazole, nystatin, ketoconazole, miconazol, etc.), antibiotic agents (penicillins, cephalosporins, erythromycin, tetracycline, aminoglycosides, etc.), antiviral agents (e.g, acyclovir, idoxuridine, etc.), breath fresheners (e.g. chlorophyll), antitussive agents (e.g., dextromethorphan hydrochloride), anti-cariogenic compounds (e.g. metallic salts of fluoride, sodium monofluorophosphate, stannous fluoride, amine fluorides), analgesic agents (e.g., methylsalicylate, salicylic acid, etc.), local anesthetics (e.g., benzocaine), oral anti-septics (e.g., chlorhexidine and salts thereof, hexylresorcinol, dequalinium chloride, cetylpyridinium chloride), anti-inflammatory agents (e.g., dexamethasone, betamethasone, prednisone, prednisolone, triamcinolone, hydrocortisone, etc.), hormonal agents (oestriol), antiplaque agents (e.g, chlorhexidine and salts thereof, octenidine, and mixtures of thymol, menthol, methylsalicylate, eucalyptol), acidity reducing agents (e.g., buffering agents such as potassium phosphate dibasic, calcium carbonate, sodium bicarbonate, sodium and potassium hydroxide, etc.), and tooth desensitizers (e.g., potassium nitrate). This list is not meant to be exclusive.

The sustained-release gel coatings of the present invention may be applied onto the active agent by preferably spraying using any suitable spray equipment known in the art. The utilization of a spray-drying technique is preferred when coating core substances comprising pellets, beads spheroids and the like. The use of any spray-drying technique allows for a more practical and uniform application of the gel coating when small-sized pellets, beads and spheroids are provided. These sustained-release gel coated pellets, beads and spheroids may be incorporated into instant release gelatin capsules (e.g., empty gel capsule) in order to further provide a more practical and dose-specific dosage form. In a preferred method, a Wurster fluidized-bed system is used in which an air jet, injected from underneath, fluidizes the core material and effects drying while the gel coating is sprayed on. A sufficient amount of the sustained-release gel coating to obtain a predetermined controlled-release of the therapeutically active agent when the coated active agent is exposed to aqueous solutions, e.g. gastric fluid, is preferably applied, taking into account the physical characteristics of the therapeutically active agent, the manner of incorporation of the plasticizer, etc.

The coated beads may be cured in order to obtain a stabilized release rate of the therapeutically active agent. The curing step may be accomplished by subjecting the coated active agent to a temperature greater than the glass transition temperature of the gel coating solution and at a relative humidity from about 60% to about 100%, until the curing endpoint is reached.

The cured, sustained-release gel coated active agents of the present invention preferably provide a dosage formulation having a stable dissolution profile (e.g., release of the active agent in the environment of use) when stored for extended periods of time at room temperature and ambient humidity (e.g., long term (real time) testing), and when tested under accelerated storage conditions.

In preferred embodiments of the present invention, the stabilized product derived from the sustained-release gel coating may be obtained by subjecting the gel coated active agent to oven curing at elevated temperature/humidity levels for the required time period, the optimum values for temperature, humidity and time for the particular formulation being determined experimentally. In certain embodiments of the present invention, the stabilized product coated with a sustained-release gel coating may be obtained via oven curing conducted at a temperature of about 60° C. and a relative humidity from about 60% to about 100% for a time period of 24 or more, e.g. up to about 72 hours. However, one skilled in the art will recognize the necessary curing conditions depending upon the particular formulation, in order to obtain a stabilized product.

In other embodiments of the present invention, there is provided an opioid analgesic dosage form useful for decreasing the potential for abuse of the opioid analgesic contained therein as described in WO 01/58451.

One method of preparing dosage forms containing sequestered opioid antagonist and releasable opioid agonist comprises preparing the antagonist in multiparticulates which are coated with a sequestering material. The sequestered multiparticulates are then mixed with a releasable opioid matrix formulation and compressed into solid dosage forms. The coatings of the present invention would provide the sequestered multiparticulates with elasticity to reduce the incidence of cracking of the multiparticulates during compression.

The gelatin/hydrophobic coated dosage forms of the present invention can be prepared utilizing the teachings of U.S. Pat. Nos. 3,959,540; 4,350,679; 4,432,768; 4,820,524; 5,146,730; 5,200,191; 5,459,983; 5,827,535; 6,183845; and 6,193,999. One skilled in the art would be able to modify the teachings of these patents in view of the present disclosure in order to include a hydrophobic material in the coatings disclosed herein, in order to prepare the sustained-release dosage forms of the present invention.

Sustained-Release Matrix Formulations

In certain embodiments, the gel coated compositions of the present invention can comprise a sustained-release matrix, e.g., sustained release opioid agonist compositions. In such embodiments, the active agent is dispersed in a sustained-release carrier to provide a matrix which provides for the sustained release, or contributes to the sustained release of the active agent from the composition.

A non-limiting list of suitable sustained-release materials which may be included in a sustained-release matrix according to the invention include hydrophilic and/or hydrophobic materials, such as gums, cellulose ethers, acrylic resins, protein derived materials, waxes, shellac, and oils such as hydrogenated castor oil and hydrogenated vegetable oil. However, any pharmaceutically acceptable hydrophobic or hydrophilic sustained-release material which is capable of imparting sustained-release of the active agent may be used in accordance with the present invention. Preferred sustained-release polymers include alkylcelluloses such as ethylcellulose, acrylic and methacrylic acid polymers and copolymers; and cellulose ethers, especially hydroxyalkylcelluloses (especially hydroxypropylmethylcellulose) and carboxyalkylcelluloses. Preferred acrylic and methacrylic acid polymers and copolymers include methyl methacrylate, methyl methacrylate copolymers, ethoxyethyl methacrylates, ethyl acrylate, trimethyl ammonioethyl methacrylate, cyanoethyl methacrylate, aminoalkyl methacrylate copolymer, poly(acrylic acid), poly (methacrylic acid), methacrylic acid alkylamine copolymer, poly(methyl methacrylate), poly(methacrylic acid)(anhydride), polymethacrylate, polyacrylamide, poly(methacrylic acid anhydride), and glycidyl methacrylate copolymers. Certain preferred embodiments utilize mixtures of any of the foregoing sustained-release materials in the matrix of the invention.

The matrix also may include a binder. In such embodiments, the binder preferably contributes to the sustained-release of the active agent from the sustained-release matrix. If an additional hydrophobic binder material is included, it is preferably selected from natural and synthetic waxes, fatty acids, fatty alcohols, and mixtures of the same. Examples include beeswax, carnauba wax, stearic acid and stearyl alcohol. This list is not meant to be exclusive. In certain preferred embodiments, a combination of two or more hydrophobic binder materials are included in the matrix formulations.

Preferred hydrophobic binder materials which may be used in accordance with the present invention include digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils, natural and synthetic waxes and polyalkylene glycols. Hydrocarbons having a melting point of between 25° and 90° C. are preferred. Of the long-chain hydrocarbon binder materials, fatty (aliphatic) alcohols are preferred in certain embodiments. The oral dosage form may contain up to 80% (by weight) of at least one digestible, long chain hydrocarbon.

In certain embodiments, the hydrophobic binder material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic acid, stearyl alcohol and hydrophobic and hydrophilic materials having hydrocarbon backbones. Suitable waxes include, for example, beeswax, glycowax, castor wax and carnauba wax. For purposes of the present invention, a wax-like substance is defined as any material which is normally solid at room temperature and has a melting point of from about 30 to about 100° C. In certain preferred embodiments, the dosage form comprises a sustained release matrix comprising the active agent and at least one water soluble hydroxyalkylcellulose, at least one $C_{12}$-$C_{36}$, preferably $C_{14}$-$C_{22}$, aliphatic alcohol and, optionally, at least one polyalkylene glycol. The hydroxyalkylcellulose is preferably a hydroxy($C_1$ to $C_6$)alkylcellulose, such as hydroxypropylcellulose, hydroxypropylmethylcellulose and, especially, hydroxyethylcellulose. The amount of the at least one hydroxyalkyl cellulose in the present oral dosage form may be determined, inter alia, by the precise rate of active agent release required. The aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the aliphatic alcohol in the present oral dosage form may be determined, as above, by the precise rate of active agent release required. It may also depend on whether at least one polyalkylene glycol is present in or absent from the oral dosage form. In the absence of at least one polyalkylene glycol, the oral dosage form preferably contains between about 20% and about 50% (by wt) of the aliphatic alcohol. When a polyalkylene glycol is present in the oral dosage form, then the combined weight of the aliphatic alcohol and the polyalkylene glycol preferably constitutes between about 20% and about 50% (by wt) of the total dosage form.

In one preferred embodiment, the ratio of, e.g., the at least one hydroxyalkyl cellulose or acrylic resin to the at least one aliphatic alcohol/polyalkylene glycol determines, to a considerable extent, the release rate of the active agent from the formulation. In certain embodiments, a ratio of the hydroxyalkyl cellulose to the aliphatic alcohol/polyalkylene glycol of between 1:1 and 1:4 is preferred, with a ratio of between 1:2 and 1:3 being particularly preferred.

In certain embodiments, the polyalkylene glycol may be, for example, polypropylene glycol, or polyethylene glycol which is preferred. The average molecular weight of the at least one polyalkylene glycol is preferably between 1,000 and 15,000, especially between 1,500 and 12,000.

Another suitable sustained-release matrix comprises an alkylcellulose (especially ethylcellulose), a $C_{12}$ to $C_{36}$ aliphatic alcohol and, optionally, a polyalkylene glycol. In addition to the above ingredients, a sustained-release matrix may also contain suitable quantities of other materials, e.g., diluents, lubricants, binders, granulating aids, colorants, flavorants and glidants that are conventional in the pharmaceutical art.

The sustained-release matrix which is included in the present gel coated dosage form can be prepared, for example, by (a) forming granules comprising at least one hydrophobic and/or hydrophilic material as set forth above (e.g., a water soluble hydroxyalkyl cellulose) together with the active agent; (b) mixing the at least one hydrophobic and/or hydrophilic material-containing granules with at least one $C_{12}$-$C_{36}$ aliphatic alcohol, and (c) optionally compressing and shaping the granules.

The granules may be formed by any of the procedures well-known to those skilled in the art of pharmaceutical formulation. For example, in one preferred method, the granules may be formed by wet granulating hydroxyalkyl cellulose and the active agent with water. In a particularly preferred embodiment of this process, the amount of water added during the wet granulation step is preferably between 1.5 and 5 times, especially between 1.75 and 3.5 times, the dry weight of the active agent.

A sustained-release matrix can also be prepared by, e.g., melt-granulation or melt-extrusion techniques. Generally, melt-granulation techniques involve melting a normally solid hydrophobic binder material, e.g., a wax, and incorporating a powdered drug therein. To obtain a sustained release dosage form, it may be necessary to incorporate a hydrophobic sustained-release material, e.g. ethylcellulose or a water-insoluble acrylic polymer, into the molten wax hydrophobic binder material.

The additional hydrophobic binder material may comprise one or more water-insoluble wax-like thermoplastic substances possibly mixed with one or more wax-like thermoplastic substances being less hydrophobic than said one or more water-insoluble wax-like substances. In order to achieve sustained release, the individual wax-like substances in the formulation should be substantially non-degradable and insoluble in gastrointestinal fluids during the initial release phases. Useful water-insoluble wax-like binder substances may be those with a water-solubility that is lower than about 1:5,000 (w/w).

The preparation of a suitable melt-extruded matrix for inclusion in the present invention may, for example, include the steps of blending the active agent, together with a sustained release material and preferably a binder material to obtain a homogeneous mixture. The homogeneous mixture is then heated to a temperature sufficient to at least soften the mixture sufficiently to extrude the same. The resulting homogeneous mixture is then extruded, e.g., using a twin-screw extruder, to form strands. The extrudate is preferably cooled and cut into multiparticulates by any means known in the art. The matrix multiparticulates are then divided into unit doses. The extrudate preferably has a diameter of from about 0.1 to about 5 mm and provides sustained release of the active agent for a time period of at least about 24 hours.

An optional process for preparing the melt extruded formulations of the present invention includes directly metering into an extruder a hydrophobic sustained release material, the oxycodone or salt thereof, and an optional binder material; heating the homogenous mixture; extruding the homogenous mixture to thereby form strands; cooling the strands containing the homogeneous mixture; cutting the strands into matrix multiparticulates having a size from about 0.1 mm to about 12 mm.

Plasticizers, such as those described above, may be included in melt-extruded matrices. The plasticizer is preferably included as from about 0.1 to about 30% by weight of the matrix. Other pharmaceutical excipients, e.g., talc, mono or polysaccharides, colorants, flavorants, lubricants and the like may be included in the sustained release matrices of the present invention as desired. The amounts included will depend upon the desired characteristic to be achieved. The diameter of the extruder aperture or exit port can be adjusted to vary the thickness of the extruded strands. Furthermore, the exit part of the extruder need not be round; it can be oblong, rectangular, etc. The exiting strands can be reduced to particles using a hot wire cutter, guillotine, etc.

A suitable amount of the multiparticulate extrudate is compressed into an oral tablet prior to the application of the gel coating. The compression can be done by using conventional tableting equipment using standard techniques, to a preferred hardness of about 2 to about 20 Kp. Techniques and compositions for making tablets (compressed and molded), capsules (hard and soft gelatin) and pills are also described in *Remington's Pharmaceutical Sciences*, (Arthur Osol, editor), 1553-1593 (1980). In yet another preferred embodiment, the extrudate can be shaped into tablets as set forth in U.S. Pat. No. 4,957,681 (Klimesch, et. al.).

In other embodiments of the invention, melt-extruded formulations are prepared without the inclusion of the active agent, which is added thereafter to the extrudate. Such formulations typically will have the active agent blended together with the extruded matrix material, and then the mixture would be tableted in order to provide a slow release formulation. Such formulations may be advantageous, for example, when the therapeutically active agent included in the formulation is sensitive to temperatures needed for softening the hydrophobic material and/or the retardant material.

Typical melt-extrusion production systems suitable for use in accordance with the present invention include a suitable extruder drive motor having variable speed and constant torque control, start-stop controls, and ammeter. In addition, the production system will include a temperature control console which includes temperature sensors, cooling means and temperature indicators throughout the length of the extruder. In addition, the production system will include an extruder such as a twin-screw extruder which consists of two counter-rotating intermeshing screws enclosed within a cylinder or barrel having an aperture or die at the exit thereof. The feed materials enter through a feed hopper and are moved through the barrel by the screws and are forced through the die into strands which are thereafter conveyed such as by a continuous movable belt to allow for cooling and being directed to a pelletizer or other suitable device to render the extruded ropes into the matrix multiparticulate system. The pelletizer can consist of rollers, fixed knife, rotating cutter and the like. Suitable instruments and systems are available from distributors such as C. W. Brabender Instruments, Inc. of South Hackensack, N.J. Other suitable apparatus will be apparent to those of ordinary skill in the art.

Alternatively, the melt-extruded product is prepared using a Werner-Pfleiderer twin screw extruder.

Optionally, the sustained-release matrix, prior to application of the gel coating, can be coated with a sustained release coating. Such coatings preferably include a sufficient amount of hydrophobic and/or hydrophilic sustained-release material to obtain a weight gain level from about 2 to about 25 percent, although the overcoat may be greater depending upon, e.g., the desired release rate. In such embodiments, the sustained-release coating may include a water insoluble material such as (a) a wax, either alone or in admixture with a fatty alcohol; or (b) shellac or zein. The coating is preferably derived from an aqueous dispersion of the hydrophobic sustained release material.

In certain embodiments, the matrix of the invention is overcoated with a sufficient amount of the aqueous dispersion of, e.g., alkylcellulose or acrylic polymer, to obtain a weight gain level from about 2 to about 50%, e.g., about 2 to about 25%, in order to obtain a sustained-release formulation. The overcoat may be lesser or greater depending upon, e.g., the desired release rate, the inclusion of plasticizer in the aqueous dispersion and the manner of incorporation of the same. Cellulosic materials and polymers, including alkylcelluloses, are sustained release materials well suited for coating the sustained release spheroids, granules, or matrix multiparticulates according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating according to the invention.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly to the matrix.

In other preferred embodiments of the present invention, the sustained release material comprising the sustained-release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in the National Formulary (NF) XVII as fully polymerized copolymers of acrylic and methacrylic acid esters with a low content of quaternary ammonium groups. In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from Röhm GMBH and Co. Kg Darmstadt, Germany. There are several different types of Eudragit®. For example, Eudragit E is an example of a methacrylic acid copolymer which swells and dissolves in acidic media. Eudragit L is a methacrylic acid copolymer which does not swell at about pH<5.7 and is soluble at about pH>6. Eudragit S does not swell at about pH<6.5 and is soluble at about pH>7. Eudragit RL and Eudragit RS are water swellable, and the amount of water absorbed by these polymers is pH-dependent; however, dosage forms coated with Eudragit RL and RS are pH-independent.

In certain preferred embodiments, the acrylic coating comprises a mixture of two acrylic resin lacquers commercially available from Rohm under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a sustained-release formulation having a desirable dis-solution profile. Desirable sustained-release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L. In embodiments of the present invention where the coating comprises an aqueous dispersion of a hydrophobic sustained release material, the inclusion of an effective amount of a plasticizer in the aqueous dispersion of hydrophobic material will further improve the physical properties of the sustained-release coating. For example, because ethylcellulose has a relatively high glass transition temperature and does not form flexible films under normal coating conditions, it is preferable to incorporate a plasticizer into an ethylcellulose coating containing sustained-release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

DETAILED DESCRIPTION OF THE INVENTION

The following examples illustrate various aspects of the present invention. They are not meant to be construed to limit the claims in any manner.

Examples 1-4 are representative of ingredients which may be used to provide for the sustained-release gel coatings of the present invention. The percentages of ingredients are representative of the dried, final coating.

EXAMPLE 1

| | |
|---|---|
| Gelatin | 40% |
| Ethylcellulose | 50% |
| Glycerin | 5% |
| Water | 5% |

EXAMPLE 2

| | |
|---|---|
| Gelatin | 35% |
| Eudragit RL/RS | 50% |
| Glycerin | 10% |
| Water | 5% |

EXAMPLE 3

| | |
|---|---|
| Gelatin | 30% |
| Ethylcellulose | 50% |
| Glycerin | 5% |
| Triethyl Citrate | 10% |
| Water | 5% |

EXAMPLE 4

| | |
|---|---|
| Gelatin | 30% |
| Eudragit RL/RS | 55% |
| Glycerin | 5% |
| Triethyl Citrate | 5% |
| Water (including coloring agent) | 5% |

The coating of examples 1-4 can enrobe a sustained-release or immediate release oxycodone matrix prepared from procedures known in the art.

EXAMPLE 5

In Example 5, a substantially non-releasable form of an opioid antagonist (naltrexone HCL) is prepared by coating naltrexone particles with a gel coating that renders the antagonist substantially non-releasable.

Naltrexone HCl 2 mg Capsules (Formulation A)

Formula:

| Ingredient | Amt/unit (mg) |
|---|---|
| Naltrexone HCl anhydrous | 2.0 |
| Eudragit RSPO | 83.0 |
| Stearyl Alcohol | 15.0 |
| Stearic Acid | 15.0 |
| Butylated Hydroxytoluene (BHT) | 1.0 |
| Gelatin | 5.0 |
| Total | 121.0 |

Process:

| | |
|---|---|
| 1. Milling | Pass stearyl alcohol flakes through a mill. |
| 2. Blending | Mix Naltrexone HCl, Eudragit, Gelatin, milled Stearyl Alcohol, Stearic Acid and BHT in a twin shell blender. |
| 3. Extrusion | Continuously feed the blended material into a twin screw extruder and collect the resultant strands on a conveyor. |
| 4. Cooling | Allow the strands to cool a Conveyor. |
| 5. Pelletizing | Cut the cooled strands into pellets using a Pelletizer. |
| 6. Screening | Screen the pellets and collect desired sieve portion. |

The gelatin coated sequestered beads can be compressed in an oxycodone matrix. When compressed under conditions to obtain a suitable pharmaceutical tablet, e.g., a target hardness of 8 kP, the beads of the naltrexone beads of the present invention would be expected to exhibit substantially less cracking as compared to compression using naltrexone beads prepared without the gelatin included in the coating.

EXAMPLE 6

Oxycodone sustained release matrix tablets are produced with the formula set forth in Table 1 below:

TABLE 1

| Ingredient | Amt/unit (mg) | Amt/batch (gram). |
|---|---|---|
| Oxycodone HCl | 30.0 | 150.0 |
| Spray Dried Lactose | 50.0 | 250.0 |

TABLE 1-continued

| Ingredient | Amt/unit (mg) | Amt/batch (gram). |
|---|---|---|
| Povidone | 8.0 | 40.0 |
| Eudragit RS30D (Solids) | 50.0 | 250.0 |
| Triacetin | 6.0 | 30.0 |
| Stearyl Alcohol | 70.0 | 350.0 |
| Talc | 4.0 | 20.0 |
| Magnesium Stearate | 2.0 | 10.0 |
| Opadry Red YS1-15597-A | 10.0 | 50.0 |
| Purified Water | * | * |
| Total | 230.0 | 1150.0 |

*Used for processing and remains in product as residual moisture only.

According to the following procedure:
1. Granulation: Spray the Eudragit/Triacetin dispersion onto the Oxycodone HCl, Spray Dried Lactose and Povidone using a fluid bed granulator.
2. Milling: Discharge the granulation and pass through a mill with approximately 1 mm openings (18 mesh screen).
3. Waxing: Melt the stearyl alcohol at about 50 degrees C. and add to the milled granulation using a high shear mixer. Allow to cool to room temperature on trays or a fluid bed.
4. Milling: Pass the cooled granulation through a mill with an approximately 18 mesh screen.
5. Lubrication: Lubricate the granulation with talc and magnesium stearate using a mixer.
6. Compression: Compress the granulation into tablets using a Kilian® Tablet press.
7. Film Coating: Apply an aqueous film coat to the tablets using a rotary pan.

The above sustained release oxycodone tablet can be enrobed with an immediate release gelatin coating to provide a tamper resistant dosage form.

EXAMPLE 7

Oxycodone 160 mg sustained release capsules are prepared with the formula set forth in Table 2 below:

TABLE 2

| Ingredient | Amt/unit (mg) |
|---|---|
| Oxycodone HCL | 160 |
| Stearic Acid | 80 |
| Stearyl Alcohol | 20 |
| Eudragit RSPO | 140 |
| Total | 400 |

The formulation above was prepared according to the following procedure:
1. Pass the stearyl alcohol flakes through an impact mill.
2. Blend the Oxycodone HCl, stearic acid, stearyl alcohol and the Eudragit RSPO in a suitable lender/mixer.
3. Continuously feed the blended material into a twin screw extruder at elevated temperatures and collect the resultant strands on a conveyor.
4. Allow the strands to cool on the conveyor.
5. Cut the strands into 1 mm pellets using a pelletizer.
6. Screen the pellets for fines and oversized pellets to an acceptable range of about 0.8-1.4 mm in size.

Prior to filling into capsules with a fill weight of 400 mg/capsule (Fill into size 00 capsules), the above sustained release oxycodone multiparticulates can be enrobed with an immediate release gelatin coating to provide a tamper resistant dosage form.

Optionally, the multiparticulates can be compressed into a tablet which can be enrobed with an immediate release gelatin coating to provide a tamper resistant dosage form.

EXAMPLE 8

Morphine Sulfate Controlled Release Capsules

FORMULA:

| | Ingredients | Amt/unit* (mg) |
|---|---|---|
| Step 1. Drug loading | Morphine sulfate | 60.0 |
| | Lactose impalpable | 12.0 |
| | Eudragit RS30D | 2.0 |
| | Povidone | 3.5 |
| | Nupareil PG 30/35 | 16.8 |
| | Opadry blue | 4.9 |
| | Water | |
| Step 2. Controlled Release Coat | MSIR beads (step 1) | 99.2 |
| | Eudragit RS 30D | 4.712 |
| | Eudragit RL 30D | 0.248 |
| | Triethyl citrate | 0.992 |
| | Talc | 1.884 |
| | Opadry blue | 5.639 |
| | Water | |
| Step 3. Encapsulation | MSCR beads (above) | 212 |

Manufacturing Procedure
1. Disperse povidone and Eudragit RS30D in water. Blend morphine sulfate and lactose.
2. Load beads in Rotor processor. Spray the drug powder blend and the binder solution onto beads.
3. Film-coat the above beads in the Rotor processor.
4. Disperse Eudragit RS30D, RL30D, Triethyl citrate, talc and triethyl citrate in water. Coat the above beads in a fluid bed coated with Wurster insert.
5. Cure the beads (MSCR beads).

Prior to filling into capsules, the above sustained release morphine sulphate multiparticulates can be enrobed with an immediate release gelatin coating to provide a tamper resistant dosage form.

What is claimed is:

1. An oral pharmaceutical dosage form comprising an active agent and a sustained-release coating disposed about the active agent, wherein the sustained-release coating comprises a pharmaceutically acceptable mixture of gelatin and hydrophobic polymer, and the hydrophobic polymer is present in an amount of at least 20% based on the total weight of the coating, wherein said dosage form provides sustained release of said active agent over at least 8 hours.

2. An oral pharmaceutical dosage form comprising an active agent and a sustained-release coating disposed about the active agent, wherein the sustained-release coating comprises a pharmaceutically acceptable mixture of gelatin and acrylic polymer.

3. An oral pharmaceutical dosage form comprising a plurality of inert beads, a first layer comprising an active agent disposed about the inert beads, and a second layer comprising a sustained-release coating comprising a pharmaceutically acceptable mixture of gelatin and hydrophobic polymer disposed about the first layer.

4. The dosage form of claim 1, wherein said hydrophobic polymer comprises a cellulosic polymer.

5. The dosage form of claim 4, wherein said cellulosic polymer is selected from the group consisting of cellulosesters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate, cellulose acetate butyrate and mixtures thereof.

6. The dosage form of claim 4, wherein said cellulosic polymer comprises ethycellulose.

7. The dosage form of claim 2, wherein said acrylic polymer is selected from the group consisting of acrylic acid and methacrylic acid copolymers, methacrylic acid copolymers, methyl methacrylate copolymers, ethoxyethyl methacrylates, cyanoethyl methacrylate, methyl methacrylate, copolymers, methacrylic acid copolymers, methyl methacrylate copolymers, methyl methacrylate copolymers, methyl methacrylate copolymers, methacrylic acid copolymer, aminoalkyl methacrylate copolymer, methacrylic acid copolymers, methyl methacrylate copolymers, poly(acrylic acid), poly(methacrylic acid, methacrylic acid alkylamide copolymer, poly (methyl methacrylate), poly(methacrylic acid) (anhydride), methyl methacrylate, polymethacrylate, methyl methacrylate copolymer, poly(methyl methacrylate), poly(methyl methacrylate) copolymer, polyacrylamide, aminoalkyl methacrylate copolymer, poly(methacrylic acid anhydride), glycidyl methacrylate copolymers and mixtures of any of the foregoing.

8. The dosage form of claim 1, wherein said hydrophobic polymer is present in an amount from 20 to about 80% based on the total weight of the sustained-release coating.

9. The dosage form of claim 2, wherein said acrylic polymer is present in an amount from about 20 to about 80% based on the total weight of the sustained-release coating.

10. The dosage form of claim 9, wherein said acrylic polymer is present in an amount from about 40 to about 60% based on the total weight of the sustained-release coating.

11. The dosage form of claim 1, further comprising a plasticizer.

12. The dosage form of claim 11, wherein said plasticizer is selected from the group consisting of hygroscopic plasticizers, non-hygroscopic plasticizers, diethyl phthalate, triethyl citrate, citric acid, mineral oil, lanolin alcohol, petroleum and lanolin alcohols and any mixtures thereof.

13. The dosage form of claim 12, wherein said hygroscopic plasticizer is selected from the group consisting of glycerin, sorbitol, and alkylene glycols.

14. The dosage form of claim 12, wherein said non-hygroscopic plasticizer is selected from the group consisting of maltitol, lactitol, xylitol, hydrogenated starch hydrosylate and partially dehydrogenated glucose syrups.

15. The dosage form of claim 11, wherein said plasticizer is present in an amount from about 5 to about 35% based on the total weight of the sustained-release coating.

16. The dosage form of claim 11, wherein said plasticizer and said gelatin are present in said sustained-release coating in a ratio from about 1:3 to 1:15.

17. The dosage form of claim 11, wherein said plasticizer and said gelatin are present in said sustained-release coating in a ratio of about 1:5.

18. The dosage form of claim 1, wherein said gelatin is present in an amount from about 0.1% to about 60%, based on the total weight of the sustained-release coating.

19. The dosage form of claim 18, wherein said gelatin is present in an amount from about 1% to 20%, based on the total weight of the sustained-release coating.

20. The dosage form of claim 18, wherein said gelatin is present in an amount from about 30 to 60%, based on the weight of the sustained-release coating.

21. The dosage form of claim 1, in the form of a tablet, a capsule, a caplet, spheroids, drug coated beads, microspheres, multiparticulate matrices, or ion-exchange resin beads.

22. The dosage form of claim 1, further comprising a matrix comprising said active agent dispersed therein.

23. The dosage form of claim 1, further comprising a plurality of matrices comprising said active agent dispersed therein.

24. The dosage form of claim 1, wherein said dosage form provides sustained release of said active agent over at least 18 hours.

25. The dosage form of claim 1, wherein said sustained-release coating has a thickness from about 5 to 50 mils.

26. The dosage form of claim 25, wherein said sustained-release coating has a thickness from about 10 to 30 mils.

27. The dosage form of claim 26, wherein said sustained-release coating has a thickness from about 15 to 25 mils.

28. The dosage form of claim 1, wherein said sustained-release coating is applied as an aqueous dispersion.

29. The dosage form of claim 1, wherein said active agent comprises an opioid agonist.

30. The dosage form of claim 29 wherein said opioid agonist is selected from the group consisting of morphine, hydromorphone, hydrocodone, oxycodone, codeine, levorphanol, meperidine, methadone, oxymorphone, buprenorphine, fentanyl and derivatives thereof, dipipanone, tramadol, etorphine, dihydroetorphine, butorphanol, levorphanol, pharmaceutically acceptable salts thereof and mixtures thereof.

31. The dosage form of claim 30, wherein the opioid agonist is selected from the group consisting of oxycodone, hydrocodone and pharmaceutically acceptable salts thereof.

32. The dosage form of claim 1, wherein said active agent comprises an opioid antagonist.

33. The dosage form of claim 32, wherein said opioid antagonist is selected from the group consisting of naltrexone, naloxone, nalmephene, cyclazocine, levallorphan, pharmaceutically acceptable salts thereof and mixtures thereof.

34. The dosage form of claim 33, wherein the opioid antagonist comprises naltrexone or a pharmaceutically acceptable salt thereof.

35. The dosage form of claim 3 wherein the mean outer diameter of the second layers is about 0.1 mm to about 3 mm.

36. The dosage form of claim 21, wherein said active agent is an opioid antagonist.

37. The dosage form of claim 36, wherein said opioid antagonist is selected from the group consisting of naltrexone, naloxone, nalmephene, cyclazocine, levallorphan, pharmaceutically acceptable salts thereof and mixtures thereof.

38. A dosage form of claim 1, wherein the active agent is in the form of a liquid or semi-solid composition.

39. A dosage form of claim 1, wherein the active agent is in the form of a solid composition.

40. An oral pharmaceutical dosage form comprising an inert core, a first layer and a second layer, the first layer being between the core and the second layer, the first layer comprising naltrexone hydrochloride and the second layer comprising a sustained release coating comprising a mixture of gelatin and hydrophobic polymer.

41. An oral pharmaceutical dosage form comprising an inert core, a first layer, a second layer and a third layer, the first layer being between the core and the second layer, the second layer being between the first layer and the third layer, the first layer comprising naltrexone hydrochloride, the second layer comprising hydrophobic polymer and the third layer comprising a sustained-release coating comprising a mixture of gelatin and hydrophobic polymer.

42. An oral pharmaceutical dosage form comprising about 10 mg oxycodone hydrochloride, less than about 5.0 mg naltrexone hydrochloride and a sustained-release coating comprising a mixture of gelatin and hydrophobic polymer.

43. An oral pharmaceutical dosage form comprising a first component comprising about 10 mg oxycodone hydrochloride, and a second component comprising less than about 5.0 mg naltrexone hydrochloride and a sustained-release coating comprising a mixture of gelatin and hydrophobic polymer.

44. An oral pharmaceutical dosage form comprising about 20 mg oxycodone hydrochloride, less than about 5.0 mg naltrexone hydrochloride and a sustained-release coating comprising a mixture of gelatin and hydrophobic polymer.

45. An oral pharmaceutical dosage form comprising a first component comprising about 20 mg oxycodone hydrochloride, and a second component comprising less than about 5.0 mg naltrexone hydrochloride and a sustained-release coating comprising a mixture of gelatin and hydrophobic polymer.

46. An oral pharmaceutical dosage form comprising about 40 mg oxycodone hydrochloride, less than about 5.0 mg naltrexone hydrochloride and a sustained-release coating comprising a mixture of gelatin and hydrophobic polymer.

47. An oral pharmaceutical dosage form comprising a first component comprising about 40 mg oxycodone hydrochloride, and a second component comprising less than about 5.0 mg naltrexone hydrochloride and a sustained-release coating comprising a mixture of gelatin and hydrophobic polymer.

48. The dosage form of claim 43, wherein the second component comprising an inert core, a first layer and a second layer, the first layer being between the core and the second layer, the first layer comprising said naltrexone hydrochloride and the second layer comprising said sustained-release coating.

49. The dosage form of claim 43, wherein the second component comprises an inert core, a first layer, a second layer and a third layer, the first layer being between the core and the second layer, the second layer being between the first layer and the third layer, the first layer comprising naltrexone hydrochloride, the second layer comprising a hydrophobic polymer and the third layer comprising said sustained-release coating.

50. An oral pharmaceutical dosage form comprising about 5-20 mg hydrocodone bitartrate, less than about 5.0 mg naltrexone hydrochloride and a sustained-release coating comprising a mixture of gelatin and hydrophobic polymer.

51. An oral pharmaceutical dosage form comprising a first component comprising about 5-20 mg hydrocodone bitartrate, and a second component comprising less than about 5.0 mg naltrexone hydrochloride and a sustained-release coating comprising a mixture of gelatin and hydrophobic polymer.

52. An oral pharmaceutical dosage form comprising a sustained release substrate comprising a matrix comprising an opioid agonist; and a sustained-release coating comprising a mixture of gelatin and a hydrophobic polymer disposed about said substrate.

53. The dosage form of claim 52, wherein said matrix is a sustained release matrix and further comprises a hydrophobic material.

54. The dosage form of claim 52, wherein said matrix is an immediate release matrix and said substrate further comprises a sustained release coating disposed about said matrix.

55. The dosage form of claim 53, wherein said substrate further comprises a sustained-release coating disposed about said sustained-release matrix.

56. The dosage form of claim 52, further comprising a protective coating disposed between said substrate and said sustained-release coating.

57. The dosage form of claim 54, further comprising a protective coating disposed between said matrix and said sustained release coating.

58. The dosage form of claim 54, further comprising a protective coating disposed between said sustained release coating and said gelatin coating.

59. The dosage form of claim 52, wherein said substrate provides a sustained release of said opioid agonist for at least 8 hours.

60. The dosage form of claim 52, wherein said substrate provides a sustained release of said opioid agonist for at least 18 hours.

61. The dosage form of claim 52, wherein said sustained-release coating has a thickness from about 5 to 100 mils.

62. The dosage form of claim 52, wherein said sustained-release coating has a thickness from about 60 to 100 mils.

63. The dosage form of claim 52, wherein said sustained-release coating has a thickness from about 15 to 40 mils.

64. The dosage form of claim 52, wherein said opioid agonist is selected from the group consisting of morphine, hydromorphone, hydrocodone, oxycodone, codeine, levorphanol, meperidine, methadone, oxymorphone, buprenorphine, fentanyl and derivatives thereof, dipipanone, tramadol, etorphine, dihydroetorphine, butorphanol, levorphanol, pharmaceutically acceptable salts thereof and mixtures thereof.

65. The dosage form of claim 52, wherein said opioid agonist is selected from the group consisting of oxycodone, pharmaceutically acceptable salts thereof and mixtures thereof.

66. An oral pharmaceutical dosage form comprising a plurality of inert beads, a first layer comprising an active agent selected from the group consisting of an opioid agonist, an opioid antagonist and a mixture thereof, said active agent disposed about the inert beads, a second layer comprising a hydrophobic polymer disposed about the first layer, and a third layer comprising a sustained-release coating comprising gelatin disposed about the second layer.

67. An oral pharmaceutical dosage form comprising a plurality of matrices comprising an active agent selected from the group consisting of an opioid agonist, an opioid antagonist and a mixture thereof, said active agent at least partially interdispersed in a hydrophobic polymer; and a layer comprising a sustained-release coating comprising a mixture of gelatin and a hydrophobic polymer disposed about said matrices.

68. The dosage form of claim 66, wherein said hydrophobic polymer comprises a cellulosic polymer.

69. The dosage form of claim 68, wherein said cellulosic polymer is selected from the group consisting of cellulosesters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate, cellulose acetate butyrate and mixtures thereof.

70. The dosage form of claim 68, wherein said cellulosic polymer comprises ethycellulose.

71. The dosage form of claim 66, wherein said hydrophobic polymer comprises an acrylic polymer.

72. The dosage form of claim 71, wherein said acrylic polymer is selected from the group consisting of acrylic acid and methacrylic acid copolymers, methacrylic acid copolymers, methyl methacrylate copolymers, ethoxyethyl methacrylates, cyanoethyl methacrylate, methyl methacrylate, copolymers, methacrylic acid copolymers, methyl methacrylate copolymers, methyl methacrylate copolymers, methyl methacrylate copolymers, methacrylic acid copolymer, aminoalkyl methacrylate copolymer, methacrylic acid copolymers, methyl methacrylate copolymers, poly(acrylic acid), poly(methacrylic acid, methacrylic acid alkylamide copolymer, poly(methyl methacrylate), poly(methacrylic acid) (anhydride), methyl methacrylate, polymethacrylate, methyl methacrylate copolymer, poly(methyl methacrylate), poly (methyl methacrylate) copolymer, polyacrylamide, aminoalkyl methacrylate copolymer, poly(methacrylic acid anhydride), glycidyl methacrylate copolymers and mixtures of any of the foregoing.

73. The dosage form of claim 66, wherein said active agent is an opioid agonist.

74. The dosage form of claim 66, wherein said active agent is an opioid antagonist.

75. The dosage form of claim 73, which provides a sustained release of the opioid agonist for at least 8 hours.

76. The dosage form of claim 73, which provides a sustained release of the opioid agonist for at least 18 hours.

77. The dosage form of any one of claims 1-3, 40-47, 50-52, or 66-67, wherein said sustained-release coating is a gel coating.

* * * * *